(12) United States Patent
Pasquier et al.

(10) Patent No.: US 7,326,254 B2
(45) Date of Patent: Feb. 5, 2008

(54) MEANS AND METHOD FOR THE SIMULTANEOUS BLEACHING AND DYEING OF KERATIN FIBRES

(75) Inventors: Cécile Pasquier, Marly (CH); Caroline Kiener, Marly (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 287 days.

(21) Appl. No.: 10/530,065

(22) PCT Filed: Jan. 30, 2004

(86) PCT No.: PCT/EP2004/000816

§ 371 (c)(1),
(2), (4) Date: Mar. 24, 2005

(87) PCT Pub. No.: WO2004/078152

PCT Pub. Date: Sep. 16, 2004

(65) Prior Publication Data
US 2006/0162096 A1  Jul. 27, 2006

(30) Foreign Application Priority Data
Mar. 5, 2003  (DE) ................ 103 09 522

(51) Int. Cl.
*A61K 7/13*  (2006.01)

(52) U.S. Cl. .............. 8/405; 8/406; 8/408; 8/409; 8/573; 8/575; 8/576; 548/146

(58) Field of Classification Search ............ 8/405, 8/406, 408, 409, 573, 575, 576; 548/146
See application file for complete search history.

(56) References Cited

U.S. PATENT DOCUMENTS

| 3,634,013 A | 1/1972 | Maul et al. |
| 2004/0060124 A1 | 4/2004 | Pasquier et al. |

FOREIGN PATENT DOCUMENTS

| DE | 1 049 381 | 1/1959 |
| FR | 1 599 968 | 8/1970 |
| GB | 1 554 331 | 10/1979 |
| WO | 97/20545 | 6/1997 |
| WO | 00/76469 A1 | 12/2000 |
| WO | 02/074268 A2 | 9/2002 |
| WO | 02/074270 A1 | 9/2002 |
| WO | WO 02/074268 A2 * | 9/2002 |
| WO | 03/042199 A1 | 5/2003 |

OTHER PUBLICATIONS

STIC Search Report dated Apr. 3, 2007.*
Vorschrift in Research Disclosure, Oct. 1978, pp. 42-44, No. 17434.
Journal of Chemical Research, Synopses, 1998, pp. 12-13.

* cited by examiner

Primary Examiner—Eisa Elhilo
(74) Attorney, Agent, or Firm—Michael J. Striker

(57) ABSTRACT

The present patent application has for an object an agent for the simultaneous brightening and coloring of keratin fibers based on a coupler-developer combination that has a basic pH and contains as developer at least one heterocyclic hydrazone derivative of formula (I) or a physiologically compatible salt thereof, at least one common coupler and as oxidant at least one combination of persulfate salts and hydrogen peroxide or an addition compound thereof; a multicomponent kit and a method for coloring keratin fibers.

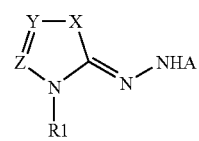

11 Claims, No Drawings

MEANS AND METHOD FOR THE SIMULTANEOUS BLEACHING AND DYEING OF KERATIN FIBRES

CROSS-REFERENCE

The invention described and claimed hereinbelow is also described in PCT/EP 2004/000816, filed on Jan. 30, 2004 and DE 103 09 522.5, filed on Mar. 5, 2003. This German Patent Application, whose subject matter is incorporated here by reference, provides the basis for a claim of priority of invention under 35 U.S.C. 119 (a)-(d).

The present invention has for an object an agent for the simultaneous brightening and coloring of keratin fibers, for example silk, wool or hair and particularly human hair, based on a developer-coupler combination containing at least one heterocyclic hydrazone derivative as developer and at least one persulfate salt and hydrogen peroxide or an addition compound thereof, and having a basic pH, as well as a method for the simultaneous brightening and coloring of keratin fibers by use of the afore-said agent.

Hair colorants are divided mainly into the groups of oxidative colorants or of tinting agents, depending on the initial color of the hair to be dyed and on the result desired. Oxidative colorants are eminently suited for covering larger gray portions. The oxidative colorants used for a 50% proportion of gray hair are as a rule referred to as oxidative tinting agents, whereas the oxidative colorants used for a greater than 50% proportion of gray hair or for "brightening" are usually referred to as oxidative dyes. Direct dyes are contained mainly in non-oxidative colorants (known as tinting agents). Because of their small [molecular] size, some direct dyes, for example nitro dyes, can penetrate into the hair and dye the hair directly, at least in the outer regions. Such tinting agents are very gentle to the hair and, as a rule, withstand 6 to 8 hair washes. Direct dyes are also often used in oxidative colorants to create certain shades or for color intensification. With the common oxidative colorants, brightening of one to two shade gradations is usually possible. For the simultaneous brightening and coloring of keratin fibers, it is also possible to use a combination of oxidation-resistant direct dyes and oxidants. Such agents are described, for example, in WO 97/20545 or WO 02/074270. Compared to colorations achieved with oxidative colorants, however, the colorations obtained with the direct dyes are usually somewhat less durable.

Hence, the purpose of the present invention is to provide a colorant for keratin fibers that gives colorations that are stable at a basic pH, that permit brightening of up to four shade gradations and that give fashionable shades as well as natural ones.

The present invention therefore has for an object a ready-to-use agent for the simultaneous brightening and coloring of keratin fibers (A), for example wool, silk, or hair and particularly human hair, based on a developer-coupler combination, having a basic pH and being characterized in that it contains (a) at least one heterocyclic hydrazone derivative of formula (I) or a physiologically compatible salt thereof

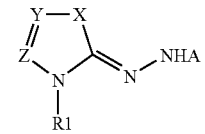

wherein
X denotes oxygen, sulfur or N—R2,
Y denotes C—R3 or nitrogen and
Z denotes C—R4 or nitrogen,
providing that the heterocyclic part of the compound of formula (I) contains at the most three heteroatoms;
A denotes hydrogen, an acetyl group, a trifluoroacetyl group, a formyl group, a ($C_1$-$C_6$)-alkylsulfonyl group or an arylsulfonyl group;
R1 and R2 can be equal or different and independently of each other denote a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a C(O)—($C_1$-$C_{12}$)-alkyl group, a C(O)-phenyl group, a C(O)NH-alkyl group, a C(O)NH-phenyl group, a substituted or unsubstituted phenyl group or a benzyl group;
R3 and R4 can be equal or different and independently of each other denote hydrogen, a halogen atom (F, Cl, Br, I), a saturated or unsaturated ($C_1$-$C_{12}$)-alkyl group, a halogen (F, Cl, Br, I)-substituted ($C_1$-$C_{12}$)-alkyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid, a C(O)O—($C_1$-$C_{12}$)-alkyl group, a substituted or unsubstituted C(O)O-phenyl group, a substituted or unsubstituted phenyl group or a naphthyl group;
and when Y and Z denote C—R3 and C—R4, R3 and R4 together with the remainder of the molecule form a heterocyclic or carbocyclic, saturated or unsaturated, substituted or unsubstituted ring system;
(b) at least one known coupler or a physiologically compatible salt thereof; and
(c) as oxidant a combination of at least one persulfate salt and hydrogen peroxide and/or an addition compound thereof.

Preferred are hydrazone derivatives of formula (I) or the physiologically compatible salts thereof wherein:
(i) X denotes sulfur, Y denotes C—R3, Z denotes C—R4 and A stands for a hydrogen atom,
or
(ii) X denotes N—R2, Y denotes nitrogen, and A stands for a hydrogen atom; the hydrazone derivatives of formula (I) or the physiologically compatible salts thereof wherein X denotes sulfur, Y denotes C—R3, Z denotes C—R4 and A stands for hydrogen being particularly preferred.

Following are examples of compounds of formula (I):
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H)-thiazolone hydrazone,
3-methyl-4-(4-tolyl)-2(3H)-thiazolone hydrazone, 4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)4-yl]-3-methyl-2(3H)-thiazolone hydrazone,
3-methyl-4-(2-naphthalenyl)-2(3H)-thiazolone,
ethyl 2-hydrazono-2,3-dihydro-3-methyl-4-thiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
3-methyl-4,5-diphenyl-2(3H)-thiazolone hydrazone,
5-ethyl-3-methyl-4-phenyl-2(3H)-thiazolone hydrazone,
4-(4-bromophenyl)-3-methyl-5-phenyl-2(3H)-thiazolone hydrazone,
3-methyl-5-phenyl-4-(4-olyl)-2(3H)-thiazolone hydrazone,
5-(4-chlorophenyl)-4-phenyl-3-methyl-2(3H)-thiazolone hydrazone,
5-(4-chlorophenyl)-4-(4-methoxyphenyl)-3-methyl-2(3H)-thiazolone hydrazone,
ethyl 2-hydrazono-2,3-dihydro-3,4-dimethyl-4-thiazolecarboxylate,
4-amino-2-hydrazono-2,3-dihydro-3-methyl-5-thiazolecarbonitrile,
3-ethyl-4,5-dimethyl-2(3H)-thiazolone hydrazone,
ethyl 2-hydrazono-2,3-dihydro-3-ethyl-4-methylthiazolecarboxylate,
5-methyl-3-(1-methylethyl)-4-phenyl-2(3H)-thiazolone hydrazone,
4,5-dimethyl-3-(1-methylethyl)-2(3H)-thiazolone hydrazone,
3-(1-methylethyl)-4,5-diphenyl-2(3H)-thiazolone hydrazone,
4,5-dimethyl-3-propyl-2(3H)-thiazolone hydrazone,
4,5-diphenyl-3-propyl-2(3H)-thiazolone hydrazone,
3-butyl-4,5-dimethyl-2(3H)-thiazolone hydrazone,
3-butyl-4,5-diphenyl-2(3H)-thiazolone hydrazone,
4,5-dimethyl-3-(2-methylpropyl)-2(3H)-thiazolone hydrazone,
3-(2-methylpropyl)-4,5-diphenyl-2(3H)-thiazolone hydrazone,
3-hydroxyethyl-2(3H)-thiazolone hydrazone,
3-hydroxyethyl-4-methyl-2(3H)-thiazolone hydrazone,
3-hydroxyethyl-4,5-dimethyl-2(3H)-thiazolone hydrazone,
3-aminoethyl-2(3H)-thiazolone hydrazone,
3-aminoethyl-4-methyl-2(3H)-thiazolone hydrazone,
3-aminoethyl-4,5-dimethyl-2(3H)-thiazolone hydrazone,
3,4-diphenyl-2(3H)-thiazolone hydrazone,
4-methyl-3-phenyl-2(3H)-thiazolone hydrazone,
4-p-biphenylyl-3-phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
4,5-dimethyl-3-phenyl-2(3H)-thiazolone hydrazone,
5-methyl-3,4-diphenyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-dimethyl-3-(2-propenyl)-2(3H)-thiazolone hydrazone,
4,5-diphenyl-3-(2-propenyl)-2(3H)-thiazolone hydrazone,
4,5-dimethyl-3-(phenylmethyl)-2(3H)-thiazolone hydrazone,
ethyl 2-hydrazono-2,3-dihydro-3-[(phenylamino)carbonyl]-4-methylthiazolecarboxylate,
3-methyl-4,5,6,7-tetrahydro-2(3H)-benzothiazolone hydrazone,
3-methyl-2(3H)-benzothiazolone hydrazone,
3,6-dimethyl-2(3H)-benzothiazolone hydrazone,
6-chloro-3-methyl-2(3H)-benzothiazolone hydrazone,
7chloro-3-methyl-2(3H)-benzothiazolone hydrazone,
6-hydroxy-3-methyl-2(3H)-benzothiazolone hydrazone,
5-methoxy-3-methyl-2(3H)-benzothiazolone hydrazone,
7-methoxy-3-methyl-2(3H)-benzothiazolone hydrazone,
5,6-dimethoxy-3-methyl-2(3H)-benzothiazolone hydrazone,
5-ethoxy-3-methyl-2(3H)-benzothiazolone hydrazone,
6-ethoxy-3-methyl-2(3H)-benzothiazolone hydrazone,
3-methyl-5-nitro-2(3H)-benzothiazolone hydrazone,
3-methyl-6-nitro-2(3H)-benzothiazolone hydrazone,
5-acetamido-3-methyl-2(3H)-benzothiazolone hydrazone,
6-acetamido-3-methyl-2(3H)-benzothiazolone hydrazone,
5-anilino-3-methyl-2(3H)-benzothiazolone hydrazone,
6-anilino-3-methyl-2(3H)-benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3-dihydro-3-methyl-6-benzothiazolyl)oxy]acethydrazide,
3-methylnaphtho[2,3-d]thiazole-2(3H)-one hydrazone,
3-ethyl-2(3H)-benzothiazolone hydrazone,
6-ethoxy-3-ethyl-2(3H)-benzothiazolone hydrazone,
3-propyl-2(3H)-benzothiazolone hydrazone,
3-butyl-2(3H)-benzothiazolone hydrazone,
3-hexyl-2(3H)-benzothiazolone hydrazone,
3-hydroxyethyl-2(3H)-benzothiazolone hydrazone,
3-aminoethyl-2(3H)-benzothiazolone hydrazone,
3-p-methylbenzyl-2(3H)-benzothiazolone hydrazone,
2-hydrazono-2,3-dihydro-3-(2-hydroxyethyl)-6-benzothiazolecarboxylic acid,
2-hydrazono-2,3-dihydro-6-methoxy-3(2H)-benzothiazolepropanesulfonic acid,
6-hexadecyloxy-2-hydrazono-3(2H)-benzothiazolepropanesulfonic acid,
ethyl 2-keto-3-benzothiazoline acetate hydrazone,
3-acetyl-2(3H)-benzothiazolone hydrazone,
2-hydrazono-3(2H)-benzothiazole carboxaldehyde,
3-methyl-2(3H)-oxazolone hydrazone,
3-phenyl-2(3H)-oxazolone hydrazone,
3-methyl-2(3H)-benzoxazolone hydrazone,
3-phenyl-2(3H)-benzoxazolone hydrazone,
1,3-dimethyl-4-imidazolin-2-one hydrazone,
1,3-diethyl-4-imidazolin-2-one hydrazone,
1,3-dihydroxyethyl-4-imidazolin-2-one hydrazone,
1,3-diaminoethyl-4-imidazolin-2-one hydrazone,
1,3-dimethyl-4-methoxy4-imidazolin-2-one hydrazone, 1,3,4-trimethyl-4-imidazolin-2-one hydrazone,
1,3-dimethyl-4-phenyl-4-imidazolin-2-one hydrazone,
4-carboxy-1,3-dimethyl-4-imidazolin-2-one hydrazone,
4-amino-1,3-dimethyl-4-imidazolin-2-one hydrazone,
1,3-dimethyl-4-dimethylamino-4-imidazolin-2one hydrazone,
1,3-dimethyl-2-benzimidazolinone hydrazone,
1,3-diethyl-2-benzimidazolinone hydrazone,
1,3-dihydroxyethyl-2-benzimidazolinone hydrazone,
1,3-diaminoethyl-2-benzimidazolinone hydrazone,
1,3,5-trimethyl-2-benzimidazolinone hydrazone,
5-methoxy-1,3-dimethyl-2-benzimidazolinone hydrazone,
5-bromo-1,3-dimethyl-2-benzimidazolinone hydrazone,
4,6-dibromo-1,3-dimethyl-2-benzimidazolinone hydrazone,
5-chloro-1,3-dimethyl-2-benzimidazolinone hydrazone,
1,3-dimethyl-5-nitro-2-benzimidazolinone hydrazone,
1,3-dimethyl-6-nitro-2-benzimidazolinone hydrazone,
1,4-dimethyl-Δ2-1,2,4-triazolin-5-one hydrazone,
1,4-dihydroxyethyl-Δ2-1,2,4-triazolin-5-one hydrazone,
1,4-diaminoethyl-Δ2-1,2,4-triazolin-5one hydrazone,
1,3,4-trimethyl-Δ2-1,2,4-triazolin-5-one hydrazone,
1,4-dimethyl-3-phenyl-Δ2-1,2,4-triazolin-5-one hydrazone,
1,4-dimethyl-3-methoxy-Δ2-1,2,4-triazolin-5-one hydrazone,
1,4-dimethyl-3-dimethylamino-Δ2-1,2,4-triazolin-5-one hydrazone,
4carboxy-1,4-dimethyl-Δ2-1,2,4-triazolin-5-one hydrazone,
4-amino-1,4-dimethyl-Δ2-1,2,4-triazolin-5-one hydrazone,
4-butyl-1-methyl-3-phenyl-Δ2-1,3,4-triazolin-5-one hydrazone,
4-methyl-Δ2-1,3,4-thiadiazolin-5-one hydrazone,
4-hydroxyethyl-Δ2-1,3,4-thiadiazolin-5-one hydrazone,
4-aminoethyl-Δ2-1,3,4-thiadiazolin-5-one hydrazone,
4-methyl-2-phenyl-Δ2-1,3,4-thiadiazolin-5-one hydrazone,
2-methoxy-4-methyl-Δ2-1,3,4-thiadiazolin-5-one hydrazone,
2-anilino-4-methyl-Δ2-1,3,4-thiadiazolin-5-one hydrazone,
2-amino-4methyl-Δ2-1,3,4-thiadiazolin-5-one hydrazone,
2-dimethylamino-4-methyl-Δ2-1,3,4-thiadiazolin-5one hydrazone,
4-methyl-2-(methylthio)-Δ2-1,3,4-thiadiazolin-5-one hydrazone,
4-(5-hydrazono-4,5-dihydro-4-methyl-1,3,4-thiadiazol-2-yl)benzenesulfonyl fluoride,
4-methyl-Δ2-1,2,4-thiadiazolin-5-one hydrazone,
4-hydroxyethyl-Δ2-1,2,4-thiadiazolin-5-one hydrazone,
4-aminoethyl-Δ2-1,2,4-thiadiazolin-5-one hydrazone,
4-methyl-3phenyl-Δ2-1,2,4-thiadiazolin-5-one hydrazone,
3-methoxy-4-methyl-Δ2-1,2,4-thiadiazolin-5-one hydrazone,
3-amino-4-methyl-Δ2-1,2,4-thiadiazolin-5-one hydrazone,
3-dimethylamino-4-methyl-Δ2-1,2,4-thiadiazolin-5-one hydrazone,
3-carboxy-4-methyl-Δ2-1,2,4-triazolin-5-one hydrazone,
1,4-dimethyl-Δ2-1,2,4-triazolin-5-one hydrazone,
1,4-dihydroxyethyl-Δ2-1,2,4-triazolin-5-one hydrazone,
1,4-diaminoethyl-Δ2-1,2,4-triazolin-5-one hydrazone,
1,3,4-trimethyl-Δ2-1,2,4-triazolin-5-one hydrazone,
1,4-dimethyl-3phenyl-Δ2-1,2,4-triazolin-5-one hydrazone and
4-methyl-3-phenyl-Δ2-1,2,4-triazolin-5-one hydrazone.

Among the compounds of formula (I), the following thiazolone hydrazone derivatives are particularly preferred:
3-methyl-2(3H)-thiazolone hydrazone,
3,4-dimethyl-2(3H)-thiazolone hydrazone,
4-tert.butyl-3-methyl-2(3H)-thiazolone hydrazone,
3-methyl-4-phenyl-2(3H )-thiazolone hydrazone,
3-methyl-4-(4-tolyl)-2(3H)-thiazolone hydrazone,
4-(4-methoxy)phenyl-3-methyl-2(3H)-thiazolone hydrazone,
4-(4-ethoxy)phenyl-3-methyl-2(3H)-thiazolone hydrazone,
4-(4-bromophenyl)-3-methyl-2(3H)-thiazolone hydrazone,
4-(3-bromophenyl)-3-methyl-2(3H)-thiazolone hydrazone,
4-(4-chlorophenyl)-3-methyl-2(3H)-thiazolone hydrazone,
4-(3-chlorophenyl)-3-methyl-2(3H)-thiazolone hydrazone,
3-methyl-4-(4-nitrophenyl)-2(3H)-thiazolone hydrazone,
3-methyl-4-(3-nitrophenyl)-2(3H)-thiazolone hydrazone,
4-[(1,1'-biphenyl)-4-yl]-3-methyl-2(3H)-thiazolone hydrazone,
ethyl 2-hydrazono-2,3-dihydro-3-methylthiazolecarboxylate,
3,4,5-trimethyl-2(3H)-thiazolone hydrazone,
3,4-dimethyl-5-phenyl-2(3H)-thiazolone hydrazone,
3,5-dimethyl-4-phenyl-2(3H)-thiazolone hydrazone,
3-methyl-4,5-diphenyl-2(3H )-thiazolone hydrazone,
5-ethyl-3-methyl-4-phenyl-2(3H)-thiazolone hydrazone,
4-(4bromophenyl)-3-methyl-5-phenyl-2(3H)-thiazolone hydrazone,
3-methyl-5phenyl-4-(4-tolyl)-2(3H)-thiazolone hydrazone,
5-(4chlorophenyl)-4-phenyl-3-methyl-2(3H)-thiazolone hydrazone,
5-(4-chlorophenyl)-4-(4-methoxyphenyl)-3methyl-2(3H)-thiazolone hydrazone,
ethyl 2-hydrazono-2,3-dihydro-3,4-dimethyl-4-thiazolecarboxylate,
4-amino-2-hydrazono-2,3dihydro-3-methyl-5-thiazolecarbonitrile,
3-ethyl-4,5-dimethyl-2(3H)-thiazolone hydrazone,
ethyl 2-hydrazono-2,3-dihydro-3-ethyl-4-methylthiazolecarboxylate,
5-methyl-3-(1-methylethyl)-4-phenyl-2(3H)-thiazolone hydrazone,
4,5-dimethyl-3-(1-methylethyl)-2(3H)-thiazolone hydrazone,
3-(1-methylethyl)-4,5-diphenyl-2(3H)-thiazolone hydrazone,
4,5-dimethyl-3-propyl-2(3H)-thiazolone hydrazone,
4,5-diphenyl-3-propyl-2(3H)-thiazolone hydrazone,
3-butyl-4,5-dimethyl-2(3H)-thiazolone hydrazone,
3-butyl-4,5-diphenyl-2(3H)-thiazolone hydrazone,
4,5-dimethyl-3-(2-methylpropyl)-2(3H)-thiazolone hydrazone,
3-(2-methylpropyl)-4,5-diphenyl-2(3H)-thiazolone hydrazone,
3-(2-propenyl)-2(3H)-thiazolone hydrazone,
4-methyl-3-(2-propenyl)-2(3H)-thiazolone hydrazone,
4-tert.butyl-3-(2-propenyl)-2(3H)-thiazolone hydrazone,
4-phenyl-3-(2-propenyl)-2(3H)-thiazolone hydrazone,
4,5-dimethyl-3-(2-propenyl)-2(3H)-thiazolone hydrazone,
4,5-diphenyl-3-(2-propenyl)-2(3H)-thiazolone hydrazone,
3-hydroxyethyl-2(3H)-thiazolone hydrazone,
3-hydroxyethyl-4-methyl-2(3H)-thiazolone hydrazone,
3-hydroxyethyl-4,5-dimethyl-2(3H)-thiazolone hydrazone,
3-aminoethyl-2(3H)-thiazolone hydrazone,
3aminoethyl-4-methyl-2(3H)-thiazolone hydrazone,
3-aminomethyl-4,5-dimethyl-2(3H)-thiazolone hydrazone,
3-phenyl-2(3H)-thiazolone hydrazone,
4-methyl-3-phenyl-2(3H)-thiazolone hydrazone,
3,4-diphenyl-2(3H)-thiazolone hydrazone,
4-p-biphenylyl-3phenyl-2(3H)-thiazolone hydrazone,
4-(4-methoxy)phenyl-3-phenyl-2(3H)-thiazolone hydrazone,
4-tert.butyl-3-phenyl-2(3H)-thiazolone hydrazone,
4,5-dimethyl-3-phenyl-2(3H)-thiazolone hydrazone, 5-methyl-3,4-diphenyl-2(3H)-thiazolone hydrazone,
3,4,5-triphenyl-2(3H)-thiazolone hydrazone,
4,5-dimethyl-3-(phenylmethyl)-2(3H)-thiazolone hydrazone,
ethyl 2-hydrazono-2,3-dihydro-3-[(phenylamino)carbonyl]-4-methylthiazolecarboxylate,
3-methyl-4,5,6,7-tetrahydro-2(3H)-benzothiazolone hydrazone,
3-methyl-2(3H)-benzothiazolone hydrazone,
3,6-dimethyl-2(3H)-benzothiazolone hydrazone,
6-chloro-3-methyl-2(3H)-benzothiazolone hydrazone,
7-chloro-3-methyl-2(3H)-benzothiazolone hydrazone,
6-hydroxy-3-methyl-2(3H)-benzothiazolone hydrazone,
5-methoxy-3-methyl-2(3H)-benzothiazolone hydrazone,
7-methoxy-3-methyl-2(3H)-benzothiazolone hydrazone,
5,6-dimethoxy-3-methyl-2(3H)-benzothiazolone hydrazone,
5-ethoxy-3-methyl-2(3H)-benzothiazolone hydrazone,
6-ethoxy-3-methyl-2(3H)-benzothiazolone hydrazone,
3-methyl-5-nitro-2(3H)-benzothiazolone hydrazone,
3-methyl-6-nitro-2(3H)-benzothiazolone hydrazone,
5-acetamido-3-methyl-2(3H)-benzothiazolone hydrazone,
6-acetamido-3-methyl-2(3H)-benzothiazolone hydrazone,
5-anilino-3-methyl-2(3H)-benzothiazolone hydrazone,
6-anilino-3-methyl-2(3H)-benzothiazolone hydrazone,
2-hydrazono-2,3-dihydro-3-methyl-6-benzothiazolecarboxylic acid,
2-hydrazono-2,3-dihydro-3-methyl-4-benzothiazolesulfonic acid,
2-hydrazono-2,3-dihydro-3-methyl-5-benzothiazolesulfonic acid,
2-hydrazono-2,3-dihydro-3-methyl-6-benzothiazolesulfonic acid,
2-hydrazono-2,3-dihydro-3-methyl-7-benzothiazolesulfonic acid,
2-hydrazono-2,3-dihydro-N,N,3-trimethyl-6-benzothiazolesulfonamide,
[(2-hydrazono-2,3dihydro-3-methyl-6-benzothiazolyl)oxy]acethydrazide,
3-methylnaphtho[2,3d]thiazole-2(3H)-one hydrazone,
3-ethyl-2(3H)-benzothiazolone hydrazone,
6-ethoxy-3-ethyl-2(3H)-benzothiazolone hydrazone,
3-propyl-2(3H)-benzothiazolone hydrazone,
3-butyl-2(3H)-benzothiazolone hydrazone,
3-hexyl-2(3H)-benzothiazolone hydrazone,
3hydroxyethyl-2(3H)-benzothiazolone hydrazone,
3-aminoethyl-2(3H)-benzothiazolone hydrazone,
3-p-methylbenzyl-2(3H)-benzothiazolone hydrazone,
2-hydrazono-2,3-dihydro-3-(2-hydroxyethyl)-6-benzothiazolecarboxylic acid,
2-hydrazono-2,3-dihydro-6-methoxy-3(2H)-benzothiazolepropanesulfonic acid,
6-hexadecyloxy-2-hydrazono-3(2H)-benzothiazolepropanesulfonic acid,
ethyl 2-keto-3-benzothiazoline acetate hydrazone,
3-acetyl-2(3H)-benzothiazolone hydrazone and
2-hydrazono-3(2H)-benzothiazole carboxaldehyde, Some of the compounds of formula (I) are commercially obtainable. However, they can also be prepared by methods of synthesis known from the literature, for example by the procedure described in Research Disclosure October 1978, pages 42-44, No. 17434, or in analogy with the method described in WO 02/074268 or DE 1 049 381 B, or else by the method described in the Journal of Chemical Research, Synopses (1998), pages 12-13.

Suitable as couplers are, in particular, the following compounds or salts thereof: N-(3-dimethylaminophenyl)urea, 2,6-diaminopyridine, 2-amino-4-[(2-hydroxyethyl)amino]-anisole, 2,4-diamino-1-fluoro-5-methylbenzene, 2,4-4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino]-1,5-dimethoxybenzene, 2,3-diamino-6-methoxypyridine, 3-amino-6-methoxy-2-(methylamino)pyridine, 2,6-diamino-3,5dimethoxypyridine, 3,5-diamino-2,6-dimethoxypyridine, 1,3-diaminobenzene; 2,4-diamino-1-(2-hydroxyethoxy)benzene, 1,3-diamino-4-(2,3-dihydroxypropoxy)benzene, 1,3-diamino-4-(3-hydroxypropoxy)-benzene, 1,3-diamino-4-(2-methoxyethoxy)benzene, 2,4-diamino-1,5-di(2-hydroxyethoxy)-benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)-propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5-[(2-hydroxyethyl)amino]-2-methylphenol, 3-[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

Suitable persulfate salts are, for example, potassium persulfate, sodium persulfate or ammonium persulfate or mixtures thereof.

The ready-to-use colorant (A) contains the persulfate salts in a total amount from about 0.01 to 10 weight percent and preferably from about 0.1 to 5 weight percent.

The hydrogen peroxide or the addition compounds thereof are contained in the ready-to-use colorant (A) in a total amount from about 1 to 10 weight percent and preferably from about 4 to 8 weight percent.

The weight ratio of persulfate salt to hydrogen peroxide in the ready-to-use colorant (A) is preferably about 1:1 to 1:20 and particularly 1:2 to 1:10.

Besides the compounds of formula (I) and the couplers, the colorant of the invention can optionally also contain other common, physiologically harmless direct dyes from the group of cationic and anionic dyes, disperse dyes, azo dyes, quinone dyes and tri-phenylmethane dyes, provided that these dyes are sufficiently stable toward the oxidants used.

The direct dyes are contained in the ready-to-use colorant (A) in an amount from about 0.01 to 10 weight percent and preferably from about 0.1 to 5 weight percent.

Besides the compounds of formula (I), the colorants of the invention can optionally contain other common developers if they are sufficiently stable toward the oxidants used.

The compounds of formula (I) and the couplers and additonal developers are contained in the ready-to-use colorant (A) in a total amount from about 0.01 to 10 weight percent, and preferably from about 0.1 to 5 weight percent, each.

As a rule, the compounds of formula (I) and the couplers are stored separately from each other and are mixed with each other only shortly before use, and then the persulfate salt and hydrogen peroxide are added. Optionally, the pH is then adjusted to the desired alkaline pH value with an alkalinizing agent. If, however, the compounds of formula (I), the couplers and the persulfate salt and optionally the other additives (for example the direct dyes and/or the additional developers) are solids, it is also possible to package them together and to prepare the ready-to-use colorant (A) shortly before use by mixing the compounds of formula (I), the couplers and the persulfate salt and the other solid additives with the hydrogen peroxide preparation and optionally with a liquid preparation containing the other ingredients of the agent.

As a rule, the colorant of the invention thus consists of several components that are mixed with each other before use. Preferably, the agent is in the form of a multicomponent kit consisting of a dye carrier composition (A1) containing the compound of formula (I), another dye carrier composition (A2) containing the couplers and the persulfate salt, and a third component (A3) containing the hydrogen peroxide and/or the addition compounds thereof, as well as optionally an agent for adjusting the pH (alkalinizing agent).

Another object of the present invention therefore is a multicomponent kit consisting of a dye carrier composition (A1) containing the compound of formula (I), another dye carrier composition (A2) containing the couplers and the persulfate salt, and a third component (A3) containing the hydrogen peroxide and/or the addition compounds thereof, as well as optionally an agent for adjusting the pH (alkalinizing agent).

Naturally, the aforesaid compositions constituting the components (A1), (A2) and (A3) can also consist of several individual components that are mixed only just before use.

Also possible is a multicomponent kit the first component of which consists of a powder containing the compound of formula (I), the couplers, the persulfate salts and optionally the alkalinizing agent, as well as other common powdered cosmetic additives, and the second component of which is an aqueous cosmetic preparation containing hydrogen peroxide and/or addition compounds thereof.

Suitable as hydrogen peroxide is an aqueous preparation (for example a solution or emulsion) containing from 1 to 12 weight percent and preferably from 6 to 9 weight percent of hydrogen peroxide or of a compound of addition thereof to urea, melamine, sodium borate or sodium carbonate.

The weight ratio of dye carrier composition to hydrogen peroxide preparation is preferably about 1:1 to 1:3 and particularly 1:1 to 1:2.

The compounds of formula (I) and the couplers are contained in a particular dye carrier composition ([component (A1) or component (A2)] in a total amount from about 0.02 to 20 weight percent, and preferably from about 0.2 to 10 weight percent, each, the total amount of the compounds of formula (I) and of the couplers contained in the ready-to-use colorant (A) being about 0.01 to 10 weight percent and preferably about 0.1 to 5 weight percent, each.

The components (A1), (A2) and (A3) and the ready-to-use colorant (A) can be formulated, for example, as a solution, particularly an aqueous or aqueous-alcoholic solution, or as a cream, a gel or an emulsion. Their composition consists of a mixture of the compound of formula (I) or of the coupler and the oxidant with the additives commonly employed for such preparations.

The additives commonly used in solutions, creams, emulsions, gels or aerosol foams are, for example, solvents such as water, lower aliphatic alcohols, for example ethanol, n-propanol and isopropanol or glycols such as glycerol and 1,2-propanediol, moreover wetting agents or emulsifiers from the classes of anionic, cationic, amphoteric or nonionic surface-active substances, such as the fatty alcohol sulfates, ethoxylated fatty alcohol sulfates, alkylsulfonates, alkylbenzenesulfonates, alkyltrimethylammonium salts, alkylbetaines, ethoxylated fatty alcohols, ethoxylated nonylphenols, fatty alkanolamides, ethoxylated fatty esters, furthermore thickeners such as the higher fatty alcohols, starch or cellulose derivatives, perfumes, hair pretreatment agents, conditioners, hair swelling agents, preservatives, moreover vaselines, paraffin oil and fatty acids and also hair-care agents such as cationic resins, lanolin derivatives, cholesterol, pantothenic acid and betaine. The said constituents are employed in amounts commonly used for such purposes, for example the wetting agents and emulsifiers at a concentration from about 0.5 to 30 weight percent [always based on component (A1) or (A2)], the thickeners in an amount from about 0.1 to 25 wt. % [always based on component (A1) or (A2)] and the hair-care agents at a concentration from about 0.1 to 5.0 weight percent [always based on component (A1) or (A2)].

Moreover, the colorants can contain additional common additives, for example antioxidants such as ascorbic acid, thioglycolic acid or sodium sulfite, as well as perfume oils, penetrants, buffering systems, complexing agents, preservatives, wetting agents, emulsifiers, thickeners and hair-care agents.

Upon mixing the dye carrier composition with the oxidant, the pH of the ready-to-use colorant of the invention assumes a value that depends on the pH of the dye carrier composition, on that of the oxidant and on the mixing ratio. The ready-to-use colorant (A) has a basic pH higher than 7 and preferably from 8 to 11. The adjustment to the basic value is preferably done with ammonia, but an organic amine, for example 2-amino-2-methyl-1-propanol, tris(hydroxymethyl)aminomethane, monoethanolamine and triethanolamine or a mixture of an organic amine and ammonia can also be used for this purpose as can inorganic bases such as alkali metal hydroxides, alkaline earth metal hydroxides, alkali metal acetates, alkaline earth metal acetates, alkali metal carbonates or alkaline earth metal carbonates or the alkaline sodium silicate.

Just before use, the ready-to-use colorant is prepared by mixing the individual components [for example (A1), (A2) and (A3)]—optionally also adding an alkalinizing agent— and then applying the mixture to the fibers, particularly human hair. Depending on the color depth desired, said mixture is allowed to act for about 5 to 60 minutes and preferably about 15 to 30 minutes at a temperature from about 20 to 50° C. and particularly from about 30 to 40° C. The fibers are then rinsed with water. After the rinsing they are optionally washed with a shampoo and possibly post-rinsed with a weak organic acid, for example citric acid or tartaric acid. The keratin fibers are then dried.

The colorant of the invention produces a uniform and lasting coloration of the keratin fibers, particularly human hair, covering the entire color spectrum, the colorations distinguishing themselves by their special color intensity and brilliance.

The following examples will explain the subject matter of the invention in greater detail without limiting its scope to these examples.

EXAMPLES

Example 1a

Synthesis of 3,4-dimethyl-2(3H)-thiazolone hydrazone hydrochloride

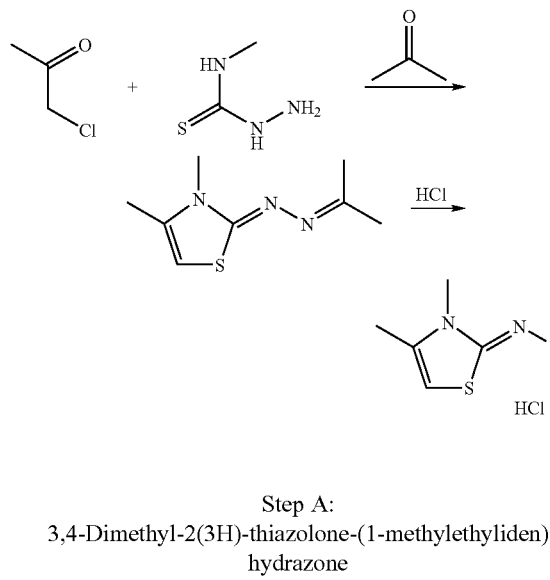

Step A:
3,4-Dimethyl-2(3H)-thiazolone-(1-methylethyliden) hydrazone 21 g (200 mmol) of 4-methyl-3-thiosemicarbazide in 1000 mL of acetone was heated at reflux for 2 hours. To the solution was then added dropwise 20.4 g (220 mmol) of chloroacetone. The reaction mixture was heated at reflux for 7 hours and concentrated. The resulting crude product was recrystallized from acetone. This gave 23 g of an orange powder (63% of the theoretical).

Melting point 139-139.6° C.

$^1$H-NMR (DMSO, 300 MHz): δ=6.72 [s, broad, 1H, H—C(5)]; δ=3.67 (s, 3H, N—CH3); δ=2.27 [d, J=0.9 Hz), 3H, CH3-C(4)]; δ=2.17 (s, 3H, CH3); δ=2.07 (s, 3H, CH3).

$^{13}$C-NMR (DMSO, 300 MHz): δ=169.16; δ=164.14; δ=139.02 [C(4)]; δ=103.36 [C(5)]; δ=34.47 (CH$_3$N); δ=24.60; δ=19.91; δ=13.53 [CH$_3$—C(4)].

MS (ESI): 184 (M$^+$+1)

Step B: 3,4-Dimethyl-2(3H)-thiazoline hydrazone hydrochloride 3.5 g (19 mmol) of 3,4-dimethyl-2(3H)-thiazolone-(1-methylethylidene) hydrazone from step A in 60 mL of 6M hydrochloric acid was heated at 50° C. for 30 minutes. The reaction mixture was then concentrated, and the crude product was recrystallized from ethanol. This gave 2 g (60% of the theoretical) of a pink powder.

Melting point 156.4-156.6° C.

$^1$H-NMR (DMSO, 300 MHz): δ=6.58 [q, J=0.9 Hz, 1H, H—C(5)]; δ=3.41 (s, 3H, N—CH3); δ=2.18 [d, J=0.9 Hz, 3H, CH3-C(4)];

MS, (ESI): 144 (M$^+$+1)

$^{13}$C-NMR (DMSO, 300 MHz): δ=172.30 [C(2)]; δ=138.79 [C(4)]; δ=101.43 [C(5)]; δ=32.92 (CH$_3$N); δ=13.40 [CH$_3$—(C4)].

CHN Analysis

[C$_5$H$_9$N$_3$S(0.96 HCl)(0.5 EtOH)]:

|  | % C | % H | % N | % S | % Cl |
|---|---|---|---|---|---|
| Calculated: | 35.81 | 6.49 | 20.88 | 15.93 | 16.90 |
| Found: | 35.20 | 6.30 | 21.00 | 15.40 | 16.80 |

Example 1b-1g

Synthesis of 2(3H) thiazolone hydrazones of Formula (I) (General Method of Synthesis)

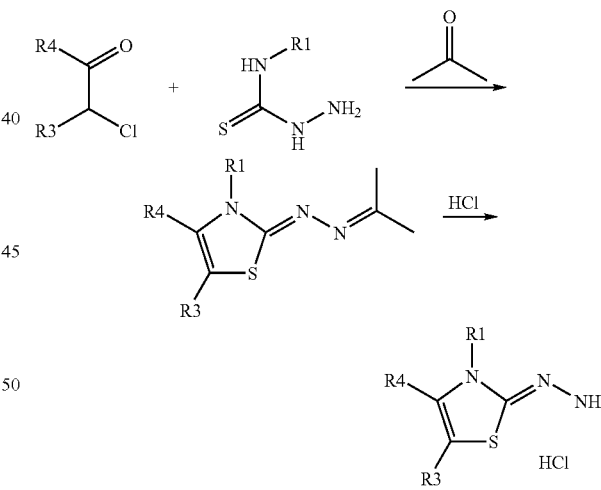

Step A: 4 mmol of substituted thiosemicarbazide in 20 mL of acetone was heated at reflux for 2 hours. To the solution was then added dropwise 4.4 mmol of a-chloroketone. The reaction mixture was heated at reflux for 7 hours and then concentrated. The resulting 2(3H)-thiazolone-1-(methylethylidene) hydrazone derivative was recrystallized from acetone.

Step B: 2 mmol of the 2(3H)-thiazolone-1-(methylethylidene) hydrazone derivative from step A in 10 mL of 6M hydrochloric acid was heated at 50° C. for 30 minutes. The reaction mixture was then concentrated, and the crude product was recrystallized from ethanol or butanol.

1b). 3-Methyl-4-phenyl-2(3H)-thiazolone hydrazone hydrochloride

From 4-methyl-3-thiosemicarbazide and phenacyl chloride.
$^1$H-NMR (DMSO/D$_2$O, 300 MHz): δ=7.49-7.42 (m, 5H, phenyl); δ=6.84 [s, 1H, H—C(5)]; δ=3.31 (s, 3H, N—CH$_3$).
ESI-MS: 205 [M]$^+$ (100)

1c.) 4-tert Butyl-3-methyl-2(3H)-thiazolone hydrazone hydrochloride

From 4-methyl-3-thiosemicarbazide and 1-chloro-3,3-dimethyl-2-butanone.
$^1$H-NMR (DMSO/D$_2$O 300 MHz): δ=6.55 [s, 1H, H—C(5)]; δ=3.60 (s, 3H, N—CH$_3$); δ=1.31 [s, 9H, (CH$_3$)$_3$].
ESI-MS: 185 [M]$^+$ (100).

1d.) 4-Methyl-3-(2-propenyl)-2(3H)-thiazolone hydrazone hydrochloride

Form 4-(2-propenyl)-3-thiosemicarbazide and chloroacetone.
$^1$H-NMR (DMSO/D$_2$O 300 MHz): δ=6.58 [s, 1H, H—C(5)]; δ=5.94-5.81 (m, 1H, allyl); δ=5.22 (dd, 1H, J=0.9 Hz, J=10.5 Hz, allyl); δ=4.94 (dd, 1H, J=0.9 Hz, J=17.1 Hz, allyl); δ=4.57 (m, 2H, N—CH$_2$); δ=2.16 [s, 3H, CH$_3$—C(4)].
ESI-MS: 169 [M]$^+$ (100).

1e.) 4-Phenyl-3-(2-propenyl)-2(3H)-thiazolone hydrazone hydrochloride

From 4-(2-propenyl)-3-thiosemicarbazide and phenacyl chloride.
$^1$H-NMR (DMSO/D$_2$O, 300 MHz): δ=7.50-7.42 (m, 5H, phenyl); δ=6.81 [s, 1H, H—C(5)]; δ=5.77-5.63 (m, 1H, allyl); δ=5.15 (dd, 1H, J=0.9 Hz, J=10.5 Hz, allyl); δ=4.80 (dd, 1H, J=0.9 Hz, J=17.1 Hz, allyl); δ=4.40 (m, 2H, N—CH$_2$); δ=1.27 [s, 9H, CH$_3$—C(4)]
ESI-MS: 231 [M]$^+$ (100).

1f.) 4-tert-Butyl 3-(2-propenyl)-2(3H)-thiazolone hydrazone hydrochloride

From 4-(2-propenyl)-3-thiosemicarbazide and 1-chloro-3,3-dimethyl-2-butanone.
$^1$H-NMR (DMSO/D$_2$O, 300 MHz): δ=6.55 [s, 1H, H—C-(5)]; δ=5.90-5.77 (m, 1H, allyl); δ=5.21 (d, 1H, J=9.0 Hz, allyl); δ=4.81-4.75 (m, 3H, allyl); δ=1.31 [s, 9H, (CH$_3$)$_3$]
ESI-MS: 211 [M]$^+$ (100).

1g.) 3,4,5-Trimethyl-2(3H)-thiazolone hydrazolone hydrochloride

From 4-methyl-3-thiosemicarbazide and 3-chloro-2-butanone.
$^1$H-NMR (DMSO/D$_2$O, 300 MHz): δ=3.55 (s, 3H, N—CH$_3$); δ=2.16 (s, 3H, CH$_3$); δ=2.12 (s, 3H, CH$_3$).
ESI-MS: 157 [M]$^+$ (100).

Examples 2-9

Colorants with 3-methyl-2(3H)-benzothiazolone hydrazone hydrochloride

Component (A1)

4.00 g of decylpolyglucose (Plantaren® 2000), aqueous solution
0.20 g of disodium ethylenediaminetetraacetate hydrate
0.50 g of ethanol
0.58 g of 3-methyl-2(3H)-benzothiazolone hydrazone hydrochloride hydrate
to 100.0 g water, demineralized Component (A2)

Y g of coupler as per Table 1
0.67 g of potassium persulfate

At room temperature (20-25° C.) or with slight heating (35-40° C.), 3.3 g of component (A1) was mixed with component (A2) and then with 6.6 g of a 9% hydrogen peroxide solution. The pH of the ready-to-use colorant (A) was adjusted to 9.5 with 25% aqueous ammonia solution. The ready-to-use hair colorant was applied to strands of natural hair and uniformly distributed with a brush. After an exposure time of 30 min at 40° C., the hair was washed with a commercial shampoo, rinsed with lukewarm water and then dried.

The amount of coupler used and the colorations obtained are summarized in the following Table 1.

TABLE 1

| Example No. | Amine or Phenol Used (Quantity in g) | Color After Dyeing |
|---|---|---|
| 2 | 1,3-diaminobenzene (0.27 g) | ruby-red |
| 3 | 2,4-diamino-1-(2-hydroxyethoxy)-benzene sulfate (0.66 g) | mahogany |
| 4 | 2-amino-4-[(2-hydroxyethyl)-amino]anisole sulfate (0.74 g) | mahogany |
| 5 | N-(3-dimethylaminophenyl)urea (0.44 g) | dark violet |
| 6 | 3-aminophenol (0.27 g) | copper-red |
| 7 | 5-amino-2-methylphenol (0.31 g) | gold-yellow |
| 8 | 1,3-dihydroxybenzene (0.27 g) | yellow-orange |
| 9 | 1-naphthol (0.36 g) | orange-red |

Examples 10-17

Colorants with 3,4-dimethyl-2(3H)-thiazolone hydrazone hydrochloride

| | Component (A1) |
|---|---|
| 4.00 g | of decylpolyglucose (Plantaren® 2000), aqueous solution |
| 0.20 g | of disodium ethylenediaminetetraacetate hydrate |
| 5.00 g | of ethanol |
| 0.45 g | of 3,4-dimethyl-2(3H)-thiazolone hydrazone hydrochloride |
| to 100.00 g | water, demineralized |
| | Component (A2) |
| Y g | of coupler as per Table 2 |
| 0.67 g | of potassium persulfate |

At room temperature (20-25° C.) or with slight heating (35-40° C.), 3.3 g of component (A1) was mixed with component (A2) and then with 6.6 g of a 9% hydrogen peroxide solution. The pH of the ready-to-use colorant (A) was adjusted to 10 with 25% aqueous ammonia. The ready-to-use hair colorant was applied to strands of natural hair and uniformly distributed with a brush. After an exposure time of 30 min at 40° C., the hair was washed with a commercial shampoo, rinsed with lukewarm water and then dried.

The amount of coupler used and the colorations obtained are summarized in the following Table 2.

TABLE 2

| Example No. | Amine or Phenol Used (Quantity in g) | Color After Dyeing |
|---|---|---|
| 10 | 1,3-diaminobenzene (0.27 g) | Bordeaux red |
| 11 | 2,4-diamino-1-(2-hydroxyethoxy)benzene sulfate (0.67 g) | dark Bordeaux red |
| 12 | 2-amino-4-[(2-hydroxyethyl)-amino]anisole sulfate (0.75 g) | dark Bordeaux red |
| 13 | N-(3-dimethylaminophenyl)urea (0.44 g) | blue |
| 14 | 3-aminophenol (0.27 g) | strawberry red |
| 15 | 5-amino-2-methylphenol (0.31 g) | copper-red |
| 16 | 1,3-dihydroxybenzene (0.27 g) | copper colors |
| 17 | 1-naphthol (0.36 g) | pink |

Examples 18-23

Colorants with 2(3H)-thiazolone hydrazone of formula (I)

| | Component (A1) |
|---|---|
| 4.00 g | of decylpolyglucose (Plantaren ® 2000), aqueous solution |
| 0.20 g | of disodium ethylenediaminetetraacetate hydrate |
| 5.00 g | of ethanol |
| 0.45 g | of 3,4-dimethyl-2(3H)-thiazolone hydrazone hydrochloride |
| to 100.00 g | water, demineralized |
| | Component (A2) |
| Y g | of coupler as per Table 2 |
| 0.67 g | of potassium persulfate |

At room temperature (20-25° C.) or with slight heating (35-40° C.), 3.3 g of component (A1) was mixed with component (A2) and then with 6.6 g of a 9% hydrogen peroxide solution. The pH of the ready-to-use colorant (A) was adjusted to 10 with 25% aqueous ammonia. The ready-to-use hair colorant was applied to strands of natural hair and uniformly distributed with a brush. After an exposure time of 30 min at 40° C., the hair was washed with a commercial shampoo, rinsed with lukewarm water and then dried.

The amount of coupler used and the colorations obtained are summarized in the following Table 3.

TABLE 3

| Example No. | Derivative of Formula (I) as per Example No. (Amount in g) | Coupler Used (Amount in g) | Color Shade |
|---|---|---|---|
| 18 | Example 1b (0.60 g) | 3-aminophenol (0.27 g) | strawberry red |
| 19 | Example 1c (0.55 g) | 3-aminophenol (0.27 g) | strawberry red |
| 20 | Example 1g (0.48 g) | 3-aminophenol (0.27 g) | Bordeaux red |
| 21 | Example 1b (0.60 g) | 5-amino-2-methyl-phenol (0.31 g) | copper-red |

TABLE 3-continued

| Example No. | Derivative of Formula (I) as per Example No. (Amount in g) | Coupler Used (Amount in g) | Color Shade |
|---|---|---|---|
| 22 | Example 1c (0.55 g) | 5-amino-2-methyl-phenol (0.31 g) | copper-red |
| 23 | Example 1g (0.48 g) | 5-amino-2-methyl-phenol (0.31 g) | copper-red |

Unless otherwise indicated, all percentages in the present patent application are by weight.

The invention claimed is:

1. Ready-to-use agent for the simultaneous brightening and coloring of keratin fibers (A), based on a developer-coupler combination and having a basic pH, said agent containing (a) at least one heterocyclic hydrazone derivative of formula (I), or a physiologically compatible salt thereof:

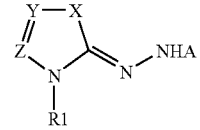

(I)

wherein
X denotes sulfur,
Y denotes C—R3 and
Z denotes C—R4,
A denotes a hydrogen atom;
R1 and R2 can be equal or different and independently of each other denote a saturated or unsaturated ($C_1$-$C_{12}$)-alkyl group, a halogen-substituted ($C_1$-$C_{12}$)-alkyl group, a hydroxy-($C_1$-$C_{12}$)-alkyl group, an amino-($C_1$-$C_{12}$)-alkyl group, a sulfonic acid-($C_1$-$C_{12}$)-alkyl group, a formyl group, a C(O)—($C_1$-$C_{12}$)-alkyl group, a C(O)-phenyl group, a C(O)NH-alkyl group, a C(O)NH-phenyl group, a substituted or unsubstituted phenyl group or a benzyl group;
R3 and R4 can be equal or different and independently of each other denote hydrogen, a halogen atom, a saturated or unsaturated ($C_1$-$C_{12}$)-alkyl group, a halogen-substituted ($C_1$-$C_{12}$)-alkyl group, a hydroxyl group, a hydroxy-($C_1$-$C_{12}$)-alkyl group, a ($C_1$-$C_{12}$)-alkoxy group, a cyano group, a nitro group, an amino group, a ($C_1$-$C_{12}$)-alkylamino group, a ($C_1$-$C_{12}$)-dialkylamino group, a carboxylic acid, a C(O)O—($C_1$-$C_{12}$)-alkyl group, a substituted or unsubstituted C(O)O-phenyl group, a substituted or unsubstituted phenyl group or a naphthyl group;
and when Y and Z denote C—R3 and C—R4, R3 and R4 together with the remainder of the molecule form a heterocyclic or carbocyclic, saturated or unsaturated, substituted or unsubstituted ring system;
(b) at least one coupler or a physiologically compatible salt thereof; and
(c) as oxidant a combination of at least one persulfate salt and hydrogen peroxide and/or an addition compound thereof,
wherein said addition compound is selected from the group consisting of an addition compound of hydrogen peroxide to urea, an addition compound of hydrogen peroxide to melamine, an addition compound of hydrogen peroxide to sodium borate and an addition compound of hydrogen peroxide to sodium carbonate.

2. Ready-to-use agent for the simultaneous brightening and coloring of keratin fibers (A) based on a developer-coupler combination and having a basic pH, containing (a) at least one heterocyclic hydrazone derivative, which is selected from the group consisting of 3-methyl-2(3H)-thiazolone hydrazone, 3,4-dimethyl-2(3H)-thiazolone hydrazone, 4-tert.butyl-3-methyl-2(3H)-thiazolone hydrazone, 3-methyl-4-phenyl-2(3H)-thiazolone hydrazone, 3-methyl-4-(4-tolyl)-2(3H)-thiazolone hydrazone, 4-(4-methoxy)phenyl-3-methyl-2(3H)-thiazolone hydrazone, 4-(4-ethoxy)phenyl-3-methyl-2(3H)-thiazolone hydrazone, 4-(4-bromophenyl)-3-methyl-2(3H)-thiazolone hydrazone, 4-(3-bromophenyl)-3-methyl-2(3H)-thiazolone hydrazone, 4-(4-chlorophenyl)-3-methyl-2(3H)-thiazolone hydrazone, 4-(3-chlorophenyl)-3-methyl-2(3H)-thiazolone hydrazone, 3-methyl-4-(4-nitrophenyl)-2(3H)-thiazolone hydrazone, 3-methyl-4-(3-nitrophenyl)-2(3H)-thiazolone hydrazone, 4-[(1,1'-biphenyl)-4-yl]-3-methyl-2(3H)-thiazolone hydrazone, 3-methyl-4-(2-naphthalenyl)-2(3H)-thiazolone hydrazone, ethyl 2-hydrazono-2,3-dihydro-3-methyl-4-thiazolecarboxylate, 3,4,5-trimethyl-2(3H)-thiazolone hydrazone, 3,4-dimethyl-5-phenyl-2(3H)-thiazolone hydrazone, 3,5-dimethyl-4-phenyl-2(3H)-thiazolone hydrazone, 3-methyl-4,5-diphenyl-2(3H)-thiazolone hydrazone, 5-ethyl-3-methyl-4-phenyl-2(3H)-thiazolone hydrazone, 4-(4-bromophenyl)-3-methyl-5-phenyl-2(3H)-thiazolone hydrazone, 3-methyl-5-phenyl-4-(4-tolyl)-2(3H)-thiazolone hydrazone, 5-(4-chlorophenyl)-4-phenyl-3-methyl-2(3H)-thiazolone hydrazone, 5-(4-chlorophenyl)-4-(4-methoxyphenyl)-3-methyl-2(3H)-thiazolone hydrazone, ethyl 2-hydrazono-2,3-dihydro-3,4-dimethyl-4-thiazolecarboxylate, 4-amino-2-hydrazono-2,3-dihydro-3-methyl-5-thiazolecarbonitrile, 3-ethyl-4,5-dimethyl-2(3H)-thiazolone hydrazone, ethyl 2-hydrazono-2,3-dihydro-3-ethyl-4-methylthiazolecarboxylate, 5-methyl-3-(1-methylethyl)-4-phenyl-2(3H)-thiazolone hydrazone, 4,5-dimethyl-3-(1-methylethyl)-4-phenyl-2(3H)-thiazolone hydrazone, 3-(1-methylethyl)-4,5-diphenyl-2(3H)-thiazolone hydrazone, 4,5-dimethyl-3-propyl-2(3H)-thiazolone hydrazone, 4,5-diphenyl-3-propyl-2(3H)-thiazolone hydrazone, 3-butyl-4,5-dimethyl-2(3H)-thiazolone hydrazone, 3-butyl-4,5-diphenyl-2(3H)-thiazolone hydrazone, 4,5-dimethyl-3-(2-methylpropyl)-2(3H)-thiazolone hydrazone, 3-(2-methylpropyl)-4,5-diphenyl-2(3H)-thiazolone hydrazone, 3-hydroxyethyl-2(3H)-thiazolone hydrazone, 3-hydroxyethyl-4-methyl-2(3H)-thiazolone hydrazone, 3-hydroxyethyl-4,5-dimethyl-2(3H)-thiazolone hydrazone, 3-aminoethyl-2(3H)-thiazolone hydrazone, 3-aminoethyl-4-methyl-2(3H)-thiazolone hydrazone, 3-aminoethyl-4,5-dimethyl-2(3H)-thiazolone hydrazone, 3,4-diphenyl-2(3H)-thiazolone hydrazone, 4-methyl-3-phenyl-2(3H)-thiazolone hydrazone, 4-p-biphenylyl-3-phenyl-2(3H)-thiazolone hydrazone, 4-(4-methoxy)phenyl-3-phenyl-2(3H)-thiazolone hydrazone, 4-tert.butyl-3-phenyl-2(3H)-thiazolone hydrazone, 4,5-dimethyl-3-phenyl-2(3H)-thiazolone hydrazone, 5-methyl-3,4-diphenyl-2(3H)-thiazolone hydrazone, 3,4,5-triphenyl-2(3H)-thiazolone hydrazone, 4,5-dimethyl-3-(phenylmethyl)-2(3H)-thiazolone hydrazone, 3-(2-propenyl)-2(3H)-thiazolone hydrazone, 4-methyl-3-(2-propenyl)-2(3H)-thiazolone hydrazone, 4-tert.butyl-3-(2-propenyl)-2(3H)-thiazolone hydrazone, 4-phenyl-3-(2-propenyl)-2(3H)-thiazolone hydrazone, 4,5-dimethyl-3-(2-propenyl)-2(3H)-thiazolone hydrazone, 4,5-diphenyl-3-(2-propenyl)-2(3H)-thiazolone hydrazone, 4,5-dimethyl-3-(phenylmethyl)-2(3H)-thiazolone hydrazone, ethyl 2-hydrazono-2,3-dihydro-3-[(phenylamino)carbonyl]-4-methylthiazolecarboxylate, 3-methyl-4,5,6,7-tetrahydro-2(3H)-benzothiazolone hydrazone, 3-methyl-2(3H)-benzothiazolone hydrazone, 3,6-dimethyl-2(3H)-benzothiazolone hydrazone, 6chloro-3-methyl-2(3H)-benzothiazolone hydrazone, 7chloro-3-methyl-2(3H)-benzothiazolone hydrazone, 6-hydroxy-3-methyl-2(3H)-benzothiazolone hydrazone, 5-methoxy-3-methyl-2(3H)-benzothiazolone hydrazone, 7-methoxy-3-methyl-2(3H)-benzothiazolone hydrazone, 5,6-dimethoxy-3-methyl-2(3H)-benzothiazolone hydrazone, 5-ethoxy-3-methyl-2(3H)-benzothiazolone hydrazone, 6-ethoxy-3-methyl-2(3H)-benzothiazolone hydrazone, 3-methyl-5-nitro-2(3H)-benzothiazolone hydrazone, 3-methyl-6-nitro-2(3H)-benzothiazolone hydrazone, 5-acetamido-3-methyl-2(3H)-benzothiazolone hydrazone, 6-acetamido-3-methyl-2(3H)-benzothiazolone hydrazone, 5-anilino-3-methyl-2(3H)-benzothiazolone hydrazone, 6-anilino-3-methyl-2(3H)-benzothiazolone hydrazone, 2-hydrazono-2,3-dihydro-3-methyl-6-benzothiazolecarboxylic acid, 2-hydrazono-2,3-dihydro-3-methyl-4-benzothiazolesulfonic acid, 2-hydrazono-2,3-dihydro-3-methyl-5-benzothiazolesulfonic acid, 2-hydrazono-2,3-dihydro-3-methyl-6-benzothiazolesulfonic acid, 2-hydrazono-2,3-dihydro-3-methyl-7-benzothiazolesulfonic acid, 2-hydrazono-2,3-dihydro-N,N,3-trimethyl-6-benzothiazolesulfonamide, [(2-hydrazono-2,3-dihydro-3-methyl-6-benzothiazolyl)oxy] acethydrazide, 3-methylnaphtho[2,3-d]thiazole-2(3H)-one hydrazone, 3-ethyl-2(3H)-benzothiazolone hydrazone, 6-ethoxy-3-ethyl-2(3H)-benzothiazolone hydrazone, 3-propyl-2(3H)-benzothiazolone hydrazone, 3-butyl-2(3H)-benzothiazolone hydrazone, 3-hexyl-2(3H)-benzothiazolone hydrazone, 3-hydroxyethyl-2(3H)-benzothiazolone hydrazone, 3-aminoethyl-2(3H)-benzothiazolone hydrazone, 3-p-methylbenzyl-2(3H)-benzothiazolone hydrazone, 2-hydrazono-2,3-dihydro-3-(2-hydroxyethyl)-6-benzothiazolecarboxylic acid, 2-hydrazono-2,3-dihydro-6-methoxy-3(2H)-benzothiazolepropanesulfonic acid, 6-hexadecyloxy-2-hydrazono-3(2H)-benzothiazolepropanesulfonic acid, ethyl 2-keto-3-benzothiazoline acetate hydrazone, 3-acetyl-2(3H)-benzothiazolone hydrazone and 2-hydrazono-3(2H)-benzothiazole carboxaldehyde;

(b) at least one coupler or physiologically compatible salt thereof; and (c) as oxidant a combination of at least one persulfate salt and hydrogen peroxide and/or an addition compound thereof;

wherein said addition compound is selected from the group consisting of an addition compound of hydrogen peroxide to urea, an addition compound of hydrogen peroxide to melamine, an addition compound of hydrogen peroxide to sodium borate and an addition compound of hydrogen peroxide to sodium carbonate.

3. Agent according to claim 1, characterized in that said at least one coupler is selected from the group consisting of N-(3-dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxy-ethoxy)-5-methylbenzene, 2,4-di[(2- hydroxyethyl)amino]-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxypyridine, 1,3-diaminobenzene, 2,4-diamino-1-(2-hydroxyethoxy)benzene, 1,3-diamino-4-(2,3-dihydroxypropoxy)benzene, 1,3-diamino-4-(3-hydroxypropoxy)-benzene, 1,3-diamino-4-(2-methoxyethoxy)benzene, 2,4-diamino-1,5-di(2-hydroxyethoxy)benzene, 1-(2-amino-ethoxy)-2,4-diaminobenzene, 2-amino-1-(2-hydroxyethoxy)-4-methylaminobenzene, 2,4-diamino-phenoxyacetic acid, 3-[di(2-hydroxyethyl)-amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxybenzene, 2,6-bis-(2-hydroxyethyl)aminotoluene, 4-hydroxyindole, 3-dimethylaminophenol, 3-diethylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlorophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]4-methoxy-2-methylphenol, 5-[(2-hydroxyethyl)amino]-2-methyl-phenol, 3-[(2-hydroxyethyl)amino]-phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 2,6-dihydroxy-3,4-dimethylpyridine, 5-amino-4-chloro-2-methyl-phenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxybenzene, 5-[(2-hydroxyethyl)amino]-1,3-benzodioxole, 6-bromo-1-hydroxy-3,4-methylenedioxybenzene, 3,4-diaminobenzoic acid, 3,4-dihydro-6-hydroxy-1,4(2H)benzoxazine, 6-amino-3,4-dihydro-1,4(2H)benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione.

4. Agent according to claim 1, characterized in that the at least one persulfate salt is selected from the group consisting of potassium persulfate, sodium persulfate and ammonium persulfate.

5. Agent according to claim 1, characterized in that the at least one heterocyclic hydrazone derivative of formula (I), the at least one coupler and the at least one persulfate salt are each contained in a total amount of 0.01 to 10 weight percent.

6. Agent according to claim 1, additionally containing from 0.01 to 10 weight percent of a physiologically harmless direct dye.

7. Agent according to claim 1, characterized in that said pH is from 7 to 10.

8. Agent according to claim 1, characterized in that it is a hair colorant.

9. Multicomponent kit consisting of a dye carrier composition (A1) containing said at least one heterocyclic hydrazone derivative of formula (I) according to claim 1, another dye carrier composition (A2) containing couplers and persulfate salts and an aqueous composition (A3) containing hydrogen peroxide or an addition compound thereof, and optionally an agent for adjusting the pH.

10. Multicomponent kit consisting of a powder (component 1) containing said at least one heterocyclic hydrazone derivative of formula (I) according to claim 1, the couplers, the persulfate salts and optionally the alkalinizing agent and other common powdered cosmetic additives, and an aqueous cosmetic preparation (component 2) containing hydrogen peroxide and/or an addition compound thereof, which is selected from the group consisting of an addition compound of hydrogen peroxide to urea, an addition compound of hydrogen peroxide to melamine, an addition compound of hydrogen peroxide to sodium borate and an addition compound of hydrogen peroxide to sodium carbonate.

11. Method for the simultaneous brightening and coloring of hair whereby a colorant according to claim 1 is applied to the hair, and after an exposure time of 5 to 60 minutes at a temperature of 20 to 50° C. the hair is rinsed with water, optionally washed with a shampoo and then dried.

* * * * *